United States Patent [19]
Clay

[11] Patent Number: 5,905,205
[45] Date of Patent: May 18, 1999

[54] BIAXIAL TESTING APPARATUS

[75] Inventor: Stephen B. Clay, Blacksburg, Va.

[73] Assignee: The United States of America as represented by the Secretary of the Air Force, Washington, D.C.

[21] Appl. No.: 09/055,614

[22] Filed: Apr. 6, 1998

[51] Int. Cl.$^6$ .................................................. G01N 3/02
[52] U.S. Cl. ................................ 73/856; 73/819; 73/853
[58] Field of Search ....................... 73/862.041, 862.042, 73/862.629, 862.635, 862.638, 862.632, 862.642, 788, 790, 796, 819, 852, 853, 856

[56] References Cited

U.S. PATENT DOCUMENTS

| | | | |
|---|---|---|---|
| 2,520,923 | 9/1950 | Franzel et al. | 73/862.635 X |
| 2,600,701 | 6/1952 | Statham et al. | 73/862.635 X |
| 2,698,371 | 12/1954 | Li | 73/862.629 |
| 2,962,893 | 12/1960 | Ormond | 73/862.642 |
| 2,986,931 | 6/1961 | Ormond | 73/862.635 |
| 2,998,584 | 8/1961 | Statham | 73/862.635 X |
| 3,230,763 | 1/1966 | Frantzis | 73/796 X |
| 3,438,251 | 4/1969 | Kloss | 73/862.642 X |
| 3,696,663 | 10/1972 | Klinger | 73/819 X |
| 3,776,028 | 12/1973 | Lynch et al. | 73/819 |
| 4,192,194 | 3/1980 | Holt . | |
| 4,885,941 | 12/1989 | Vardoulakis et al. | 73/819 X |
| 4,895,027 | 1/1990 | Manahan, Sr. | 73/799 |
| 5,144,844 | 9/1992 | Mathiak et al. . | |
| 5,279,166 | 1/1994 | Ward et al. | 73/856 X |
| 5,448,918 | 9/1995 | Tucchio | 73/819 |

Primary Examiner—Elizabeth L. Dougherty
Attorney, Agent, or Firm—Fredric L. Sinder; Thomas L. Kundert

[57] ABSTRACT

A new apparatus and method for applying a biaxial load to a flat plate test specimen is disclosed. A rhombus-shaped four-bar linkage is attached at one vertex to a fixed attachment point and a uniaxial tensile force is applied to the opposite vertex. The test specimen is placed inside the four-bar linkage and is attached to the four bar linkage by load transfer members connected at one end to the links of the four bar linkage and at their other end to grips holding the test specimen. In one embodiment, load transfer members parallel to the applied uniaxial tensile force are attached to test specimen grips adjacent to the link attachment points of the load transfer members and perpendicular load transfer members are attached to test specimen grips opposite their link attachment points. Application of the uniaxial tensile force then produces a biaxial tensile force in the test specimen. By attaching all load transfer members to test specimen grips adjacent to their link attachment points, a biaxial stress state tensile in one direction and compressive in a perpendicular direction can be accomplished.

8 Claims, 2 Drawing Sheets

BIAXIAL TESTING APPARATUS

RIGHTS OF THE GOVERNMENT

The invention described herein may be manufactured and used by or for the Government of the United States for all governmental purposes without the payment of any royalty.

BACKGROUND OF THE INVENTION

The present invention relates generally to testing apparatus, and more specifically to apparatus and methods for applying a biaxial load to a flat test specimen.

Prior art methods for applying a biaxial load to a test specimen require either two or more separate actuators, complex specimen configurations, or pressurization techniques. A common method for creating a biaxial stress state requires a loading apparatus having two orthogonally mounted actuators. A specimen is attached to the two actuators to produce loads along two orthogonal axes. A particular disadvantage of this approach is the high cost of the equipment, which often must be custom made.

A cruciform, or cross-shaped, specimen has also been used in the biaxial stress testing prior art. The orthogonal arms of the cruciform are both put under a tensile load with the central portion of the intersecting region being the test area undergoing a biaxial stress. The disadvantages of this method are that two or more loading devices are required and excess material and fabrication time are required for the specimen compared to a straightforward flat plate.

Another prior art method for biaxial loading is pressurizing the inside surface of a cylindrical specimen and applying compressive loads to the end of the specimen. One disadvantage of this method is that the specimen must be cylindrical, requiring more material and fabricating time than a simple flat plate specimen. Another disadvantage is the high cost of the equipment necessary to pressurize the cylinder.

Thus it is seen that there is a need for a simple, straightforward apparatus and method for applying a biaxial stress to a flat plate test specimen.

It is, therefore, a principal object of the present invention to provide such a simple and straightforward apparatus and method.

It is a feature of the present invention that it is compatible with conventional uniaxial test equipment.

It is an advantage of the present invention that it is inexpensive to make, to use and to fabricate test specimens.

It is another advantage of the present invention that it allows a wide variety of load combinations.

These and other objects, features and advantages of the present invention will become apparent as the description of certain representative embodiments proceeds.

SUMMARY OF THE INVENTION

In accordance with the foregoing principles and objects of the present invention, a novel apparatus and method for applying a biaxial stress to a flat plate test specimen is described. The unique discovery of the present invention is that a uniaxial tensile load can be converted to a biaxial stress state on a flat plate test specimen by use of load transfer members attached at one of each of their ends to respective links of a four-bar linkage and at their other ends to a flat plate test specimen enclosed by the four-bar linkage. By choosing the lengths of the load transfer members so that they either attach directly to adjacent sides of the test specimen, or overlap the test specimen to attach to opposite sides of the test specimen, a biaxial load will be applied to a test specimen that, depending on the selection of attachment points on the test specimen, may be compressive in two perpendicular directions, tensile in two perpendicular directions or compressive in one direction and tensile in a perpendicular direction. By varying the attachment locations of the load transfer members on the links of the four-bar linkage, different ratios between the horizontal and vertical components of a stress tensor can be achieved.

Accordingly, the present invention is directed to a test apparatus for applying a biaxial load to a test specimen, comprising a four-bar linkage for enclosing the test specimen, the four-bar linkage having a first, second, third and fourth vertex, a first link between the first and second vertices, a second link between the second and third vertices, a third link between the third and fourth vertices, and a fourth link between the fourth and first vertices, and a pair of load transfer members attached at respective first ends to the first and second links, a second pair of load transfer members opposing the first pair of load transfer members and attached at respective first ends to the third and fourth links, a third pair of load transfer members attached at respective first ends to the fourth and first links, and a fourth pair of load transfer members opposing the third pair of load transfer members and attached at respective first ends to the second and third links. The four-bar linkage may form a rhombus. The respective lengths for the first, second, third and fourth load transfer members may be such that the first and second pairs of load transfer members attach at respective second ends to sides of the test specimen adjacent to the point of attachment of the first ends of said pairs of load transfer members, and the third and fourth pairs of load transfer members attach at respective second ends to sides of the test specimen opposite the point of attachment of the first ends of said pairs of load transfer members. The respective lengths for the first, second, third and fourth load transfer members may also be such that the first and second pairs of load transfer members attach at respective second ends to sides of the test specimen adjacent to the point of attachment of the first ends of said pairs of load transfer members, and the third and fourth pairs of load transfer members attached at respective second ends to sides of the test specimen adjacent to the point of attachment of the first ends of said pairs of load transfer members.

The present invention is also directed to a method for applying a biaxial load to a test specimen, comprising the steps of enclosing the test specimen inside a four-bar linkage, wherein the four-bar linkage has a first, second, third and fourth vertex, a first link between the first and second vertices, a second link between the second and third vertices, a third link between the third and fourth vertices, and a fourth link between the fourth and first vertices, attaching each of four sides of the test specimen to, respectively, a first pair of load transfer members attached at respective first ends to the first and second links, a second pair of load transfer members opposing the first load transfer member and attached at respective first ends to the third and fourth links, a third pair of load transfer members attached at respective first ends to the fourth and first links, and a fourth pair of load transfer members opposing the third pair of load transfer members and attached at respective first ends to the second and third links, attaching the first and second pair of load transfer members at respective second ends to sides of the test specimen adjacent to the point of attachment of the first ends of said pair of load transfer members, attaching the third and fourth pair of load transfer members at respective second ends to sides of the test specimen opposite the point of attachment of the first ends of said pair of load transfer members, and while holding the first vertex in a fixed position, applying a uniaxial force to the third vertex in a direction opposite from the first vertex. The four-bar linkage may form a rhombus.

The present invention is further directed to a method for applying a biaxial load to a test specimen, comprising the steps of enclosing the test specimen inside a four-bar linkage, wherein the four-bar linkage has a first, second, third and fourth vertex, a first link between the first and second vertices, a second link between the second and third vertices, a third link between the third and fourth vertices, and a fourth link between the fourth and first vertices, attaching each of four sides of the test specimen to, respectively, a first pair of load transfer members attached at respective first ends to the first and second links, a second pair of load transfer members opposing the first load transfer member and attached at respective first ends to the third and fourth links, a third pair of load transfer members attached at respective first ends to the fourth and first links, and a fourth pair of load transfer members opposing the third pair of load transfer members and attached at respective first ends to the second and third links, attaching the first and second pair of load transfer members at respective second ends to sides of the test specimen adjacent to the point of attachment of the first ends of said pair of load transfer members, attaching the third and fourth pair of load transfer members at respective second ends to sides of the test specimen adjacent to the point of attachment of the first ends of said pair of load transfer members, and while holding the first vertex in a fixed position, applying a uniaxial force to the third vertex in a direction opposite from the first vertex.

The present invention is still further directed to a method for applying a biaxial load to a test specimen, comprising the steps of enclosing the test specimen inside a four-bar linkage, wherein the four-bar linkage has a first, second, third and fourth vertex, a first link between the first and second vertices, a second link between the second and third vertices, a third link between the third and fourth vertices, and a fourth link between the fourth and first vertices, attaching each of four sides of the test specimen to, respectively, a first pair of load transfer members attached at respective first ends to the first and second links, a second pair of load transfer members opposing the first load transfer member and attached at respective first ends to the third and fourth links, a third pair of load transfer members attached at respective first ends to the fourth and first links, and a fourth pair of load transfer members opposing the third pair of load transfer members and attached at respective first ends to the second and third links, attaching the first and second pair of load transfer members at respective second ends to sides of the test specimen opposite the point of attachment of the first ends of said pair of load transfer members, attaching the third and fourth pair of load transfer members at respective second ends to sides of the test specimen opposite the point of attachment of the first ends of said pair of load transfer members, and while holding the first vertex in a fixed position, applying a uniaxial force to the third vertex in a direction opposite from the first vertex.

BRIEF DESCRIPTION OF THE DRAWINGS

The present invention will be more clearly understood from a reading of the following detailed description in conjunction with the accompanying drawings wherein.

DETAILED DESCRIPTION

Figure 1:
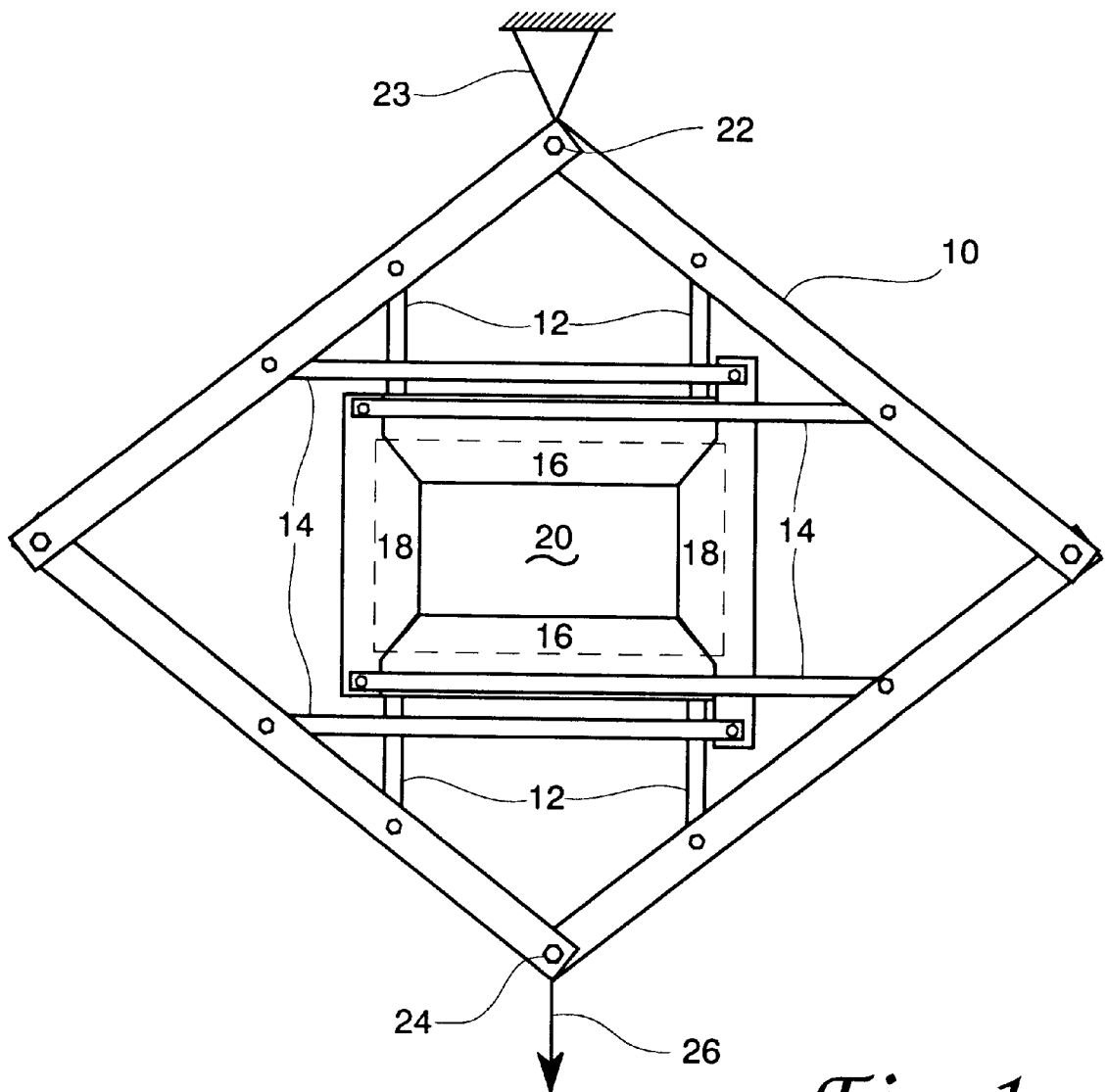
FIG. 1 is a schematic view of a four-bar linkage and associated load transfer members attached to a flat plate test specimen according to the teachings of the present invention; and, FIG. 2 is a plan view of a flat plate test specimen showing an example set of grips for attaching load transfer members to the test specimen.

Referring now to FIG. 1 of the drawings, there is shown a schematic view of a four-bar linkage 10 and associated load transfer members 12 and 14 attached to a set of grips 16 and 18 holding a flat plate test specimen 20. The main structure of the invention is four-bar linkage 10. Four-bar linkage 10 is attached at a vertex 22 to a rigid attachment point 23. A tensile force 26 is applied to a vertex 24 opposite vertex 22 to actuate four-bar linkage 10 and apply a load to test specimen 20.

Four load transfer members 12 are pinned at one of their ends to four-bar linkage 10 as shown in FIG. 1. The other ends of load transfer members 12 are attached to adjacent grips 16 to uniformly distribute a tensile load to the specimen. The other four load transfer members 14 are pinned to four-bar linkage 10 as shown and their other ends are attached to respective grips 18 on the opposite sides of flat plate specimen 20 from the four-bar linkage attachment points.

In this preferred embodiment, four-bar linkage 10 is a rhombus. Flat plate test specimen 20 is oriented so that an imaginary line passing through opposite vertices of four-bar linkage 10 will bisect the four sides of specimen 20.

This attachment arrangement converts vertical tensile force 26 into a biaxial tensile load in specimen 20. The location of vertical load transfer members 12 and horizontal load transfer members 14 with respect to their attachment points on four-bar linkage 10 determine the ratio between the horizontal and vertical components of the resulting stress in test specimen 10.

An alternative mode of the invention is to connect each horizontal load transfer member 14 to its respective adjacent specimen grip 18 rather than to its respective opposite specimen grip 18. In this configuration, a tension-compression stress state will be applied to flat plate specimen 20. Similarly, the stress state can be made compression-compression by then connecting each vertical load transfer member 12 to its respective opposite specimen grip 16 instead of to its respective adjacent specimen grip 16. Varying the connection point locations of the load transfer members with respect to linkage 10 will produce a range of ratios between the horizontal and vertical components of the stress tensor. This will allow all four quadrants of the biaxial stress tensor to be defined.

Figure 2:
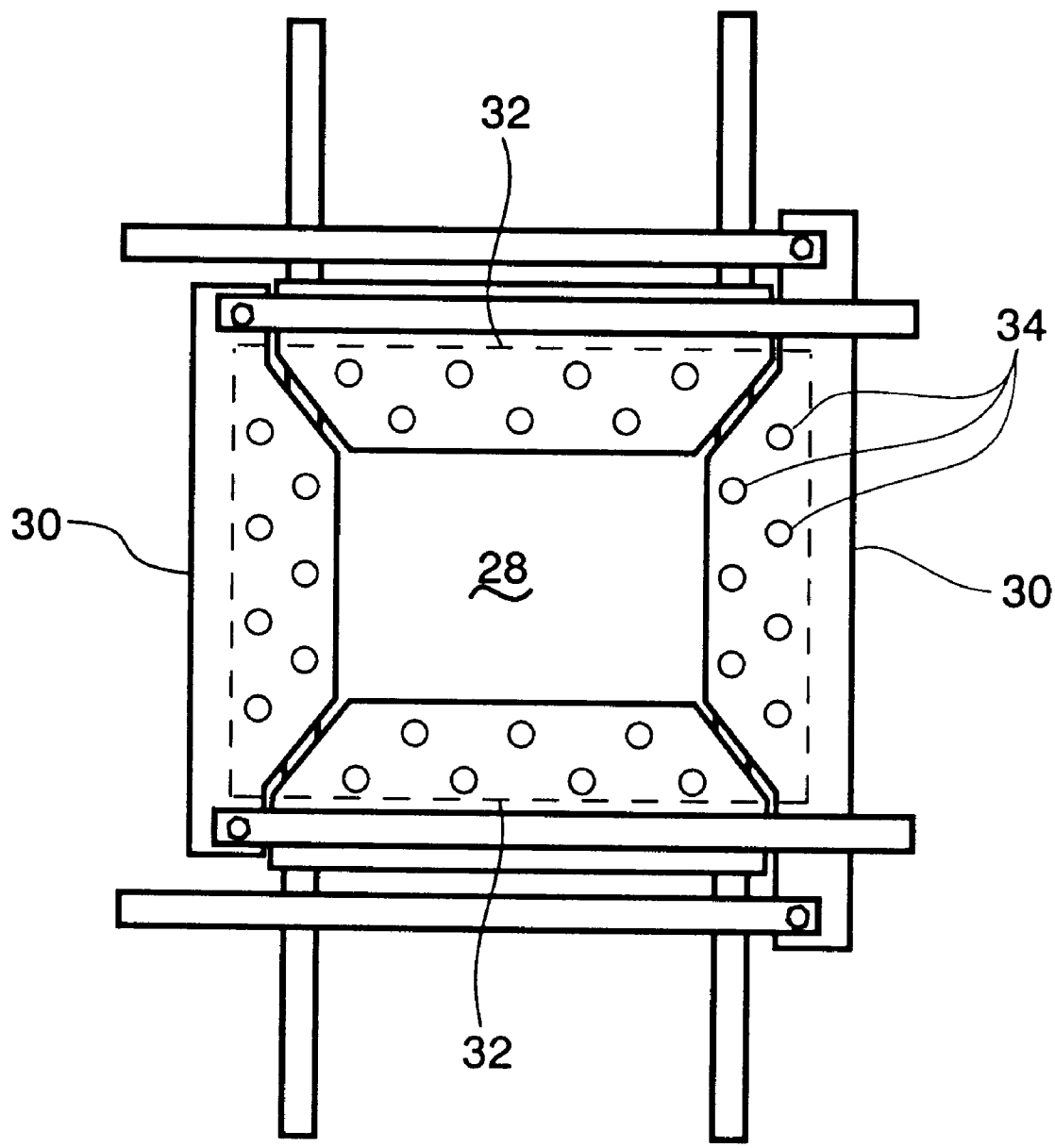

FIG. 2 is a plan view of a flat plate test specimen 28 showing an example set of grips 30 and 32 for attaching load transfer members to test specimen 28. Grips 30 and 32 each comprise a pair of grip sides on top and bottom sides of test specimen 28 to sandwich test specimen 28 and hold it in place with multiple staggered pins 34. The stress concentrations caused by pins 34 will be small far from the pin locations, most importantly in the center of specimen 28. Grips 30 and 32 are but one means for attaching load transfer members to a test specimen. One alternative method would be to use a scissors-type gripping mechanism to produce a more uniformly strained specimen.

The load transfer members do not need to be in pairs, but may be made as single units or as multi-arm units, both as functional equivalents to the described paired load transfer members. For example, the described load transfer member pairs may, depending on the exact manner in which they connect to the grips, need to comprise four arms, two each for the top and bottom of a test specimen, so that they do not impart a twist to the test specimen. The use of multi-arm load transfer members, however, is preferred because it allows for relative angular movement among the load transfer member arms. The use of a single unit load transfer member may be expected to be limited to precise positioning of the connection points of each load transfer member so that relative angular movement will not occur. Using multi-arm load transfer members permits a greater variety of configurations. Those of ordinary skill in the art will readily see other methods for attaching load transfer members to the grips. The term load transfer member as used in the claims, therefore, includes load transfer members of one or more arms and load transfer members of other configurations as might occur to one of skill in the art.

The disclosed biaxial testing apparatus and method successfully demonstrate the advantages of using a straightforward four-bar linkage as the actuating mechanism for applying a biaxial load to a test specimen. Although the disclosed invention is specialized, its teachings will find application in other areas where overly complex mechanisms are currently used for movement and force application.

Those with skill in the art of the invention will readily see other possible embodiments for the described invention. For example, the load transfer members may be connected directly to a test specimen. Although not recommended, such an arrangement will still take advantage of the teachings of the present invention. As used in the claims, therefore, any attachment to the sides of a test specimen is understood to include attachment by grips, as related in this description, by grips other than as described, by means for attaching other than grips, or by direct attachment to a test specimen. It is further understood, therefore, that modifications to the invention may be made, as might occur to one with skill in the field of this invention, within the scope of the appended claims. All embodiments contemplated have not been shown in complete detail. Other embodiments may be developed without departing from the spirit of this invention or from the scope of the claims.

I claim:

1. A test apparatus for applying a biaxial load to a test specimen, comprising:
   (a) a four-bar linkage for enclosing the test specimen, the four-bar linkage having a first, second, third and fourth vertex, a first link between the first and second vertices, a second link between the second and third vertices, a third link between the third and fourth vertices, and a fourth link between the fourth and first vertices; and,
   (b) a load transfer member attached at respective first ends to the first and second links, a second pair of load transfer members opposing the first pair of load transfer members and attached at respective first ends to the third and fourth links, a third pair of load transfer members attached at respective first ends to the fourth and first links, and a fourth pair of load transfer members opposing the third pair of load transfer members and attached at respective first end to the second and third links.

2. The test apparatus according to claim 1, wherein the four-bar linkage forms a rhombus.

3. The test apparatus according to claim 1, further comprising respective lengths for the first, second, third and fourth load transfer members such that:
   (a) the first and second pairs of load transfer members are attached at respective second ends to sides of the test specimen adjacent to the point of attachment of the first ends of said pairs of load transfer members; and,
   (b) the third and fourth pairs of load transfer members are attached at respective second ends to sides of the test specimen opposite the point of attachment of the first ends of said pairs of load transfer members.

4. The test apparatus according to claim 1, further comprising respective lengths for the first, second, third and fourth load transfer members such that:
   (a) the first and second pairs of load transfer members are attached at respective second ends to sides of the test specimen adjacent to the point of attachment of the first ends of said pairs of load transfer members; and,
   (b) the third and fourth pairs of load transfer members are attached at respective second ends to sides of the test specimen adjacent to the point of attachment of the first ends of said pairs of load transfer members.

5. A method for applying a biaxial load to a test specimen, comprising the steps of:
   (a) enclosing the test specimen inside a four-bar linkage, wherein the four-bar linkage has a first, second, third and fourth vertex, a first link between the first and second vertices, a second link between the second and third vertices, a third link between the third and fourth vertices, and a fourth link between the fourth and first vertices;
   (b) attaching each of four sides of the test specimen to, respectively, a first pair of load transfer members attached at respective first ends to the first and second links, a second pair of load transfer members opposite the first load transfer member and attached at respective first ends to the third and fourth links, a third pair of load transfer members attached at respective first ends to the fourth and first links, and a fourth pair of load transfer members opposing the third pair of load transfer members and attached at respective first ends to the second and third links;
   (c) attaching the first and second pair of load transfer members at respective second ends to sides of the test specimen adjacent to the point of attachment of the first ends of said pair of load transfer members;
   (d) attaching the third and fourth pair of load transfer members at respective second ends to sides of the test specimen opposite the point of attachment of the first ends of said pair of load transfer members; and,
   (e) while holding the first vertex in a fixed position; applying a uniaxial force to the third vertex in a direction opposite from the first vertex.

6. The method for applying a biaxial load as described in claim 5, wherein the four-bar linkage forms a rhombus.

7. A method for applying a biaxial load to a test specimen, comprising the steps of:
   (a) enclosing the test specimen inside a four-bar linkage, wherein the four-bar linkage has a first, second, third and fourth vertex, a first link between the first and second vertices, a second link between the second and third vertices, a third link between the third and fourth vertices, and a fourth link between the fourth and first vertices;
   (b) attaching each of four sides of the test specimen to, respectively, a first pair of load transfer members attached at respective first ends to the first and second links, a second pair of load transfer members opposing the first load transfer member and attached at respective first ends to the third and fourth links, a third pair of load transfer members attached at respective first ends to the fourth and first links, and a fourth pair of load transfer members opposing the third pair of load transfer members and attached at respective first ends to the second and third links;

(c) attaching the first and second pair of load transfer members at respective second ends to sides of the test specimen adjacent to the point of attachment of the first ends of said pair of load transfer members;

(d) attaching the third and fourth pair of load transfer members at respective second ends to sides of the test specimen adjacent to the point of attachment of the first ends of said pair of load transfer members; and (e) while holding the first vertex in a fixed position, applying a uniaxial force to the third vertex in a direction opposite from the first vertex.

8. A method for applying a biaxial load to a test specimen, comprising the steps of:

(a) enclosing the test specimen inside a four-bar linkage, wherein the four-bar linkage has a first, second, third and fourth vertex, a first link between the first and second vertices, a second link between the second and third vertices, a third link between the third and fourth vertices, and a fourth link between the fourth and first vertices;

(b) attaching each of four sides of the test specimen to, respectively, a first pair of load transfer members attached at respective first ends to the first and second links, a second pair of load transfer members opposing the first load transfer member and attached at respective first ends to the third and fourth links, a third pair of load transfer members attached at respective first ends to the fourth and first links, and a fourth pair of load transfer members opposing the third pair of load transfer members and attached at respective first ends to the second and third links;

(c) attaching the first and second pair of load transfer members at respective second ends to sides of the test specimen opposite the point of attachment of the first ends of said pair of load transfer members;

(d) attaching the third and fourth pair of load transfer members at respective second ends to sides of the test specimen opposite the point of attachment of the first ends of said pair of load transfer members; and (e) while holding the first vertex in a fixed position, applying a uniaxial force to the third vertex in a direction opposite from the first vertex.

* * * * *